United States Patent [19]

Auman et al.

[11] Patent Number: 5,177,179
[45] Date of Patent: Jan. 5, 1993

[54] PERFLUOROALKYLATED DIAMINOMESITYLENE AND POLYIMIDES THEREFROM

[75] Inventors: Brian C. Auman, Newark; David P. Higley, Wilmington, both of Del.; Bruce B. Johnson, Berwyn, Pa.

[73] Assignee: E. I. Du Pont de Nemours and Company, Wilmington, Del.

[21] Appl. No.: 680,445

[22] Filed: Apr. 4, 1991

[51] Int. Cl.$^5$ ............................................. C08G 69/26
[52] U.S. Cl. ................................... 528/353; 528/125; 528/126; 528/128; 528/170; 528/171; 528/172; 528/176; 528/183; 528/184; 528/185; 528/220; 528/229; 528/350; 528/351
[58] Field of Search ............... 528/353, 350, 351, 125, 528/128, 126, 170, 171, 172, 220, 229, 183, 184, 176, 185

[56] References Cited

U.S. PATENT DOCUMENTS

| | | | |
|---|---|---|---|
| 4,876,330 | 10/1989 | Higashi et al. | 528/353 |
| 4,880,895 | 11/1989 | Higashi et al. | 528/173 |

FOREIGN PATENT DOCUMENTS

| | | |
|---|---|---|
| 1180860 | 7/1989 | Japan. |
| 1190652 | 7/1989 | Japan. |
| 2-60933 | 3/1990 | Japan. |

*Primary Examiner*—John Kight, III
*Assistant Examiner*—P. Hampton-Hightower

[57] ABSTRACT

Perfluoroalkylated diaminoesitylene and polymers, preferably polyimides, made therefrom. The necessarily obtainable meta-substitution position of the perfluoroalkyl group with respect to both amino-groups provides an improved diamine and compositions of matter resulting therefrom.

9 Claims, No Drawings

PERFLUOROALKYLATED DIAMINOMESITYLENE AND POLYIMIDES THEREFROM

1. Field of the Invention

This invention relates to perfluoroalkylated diamines, and more particularly to perfluoroalkyldiaminomesitylene and polymers, preferably polyimides, made therefrom.

2. Background of the Invention

Polyimides represent an important class of high-temperature polymers with a broad range of applications. In the electronics industry, they are used in many applications which take advantage of their thermal stability, good electrical properties and other very useful characteristics. Polyimides, however, tend to absorb moisture, which results in changes in electrical properties under varied humidity conditions. Additionally, as the drive in electronics for smaller size continues, materials with improved dielectric properties, e.g., lower dielectric constant, are required.

Fluorination has been used to reduce both moisture absorption and dielectric constant in polyimides. For example, Japanese Patent Application Publication (Kokai) No. 1-190652 (Appl. No. 63-12660), Japanese Patent Application Publication (Kokai) No. Hei 2-60933 (Appl. No. 63-211799), and Japanese Patent Application Publication (Kokai) No. Hei 1-18860 (Appl. No. 63-4760) disclose use of perfluoroalkyldiaminobenzene in preparing polyimides. However, the raw materials for preparing such diamines are not readily available, and thus, it is not easy to prepare the most stable homologue, which has all three groups (the two amine groups and the perfluoroalkyl group) in meta position with respect to each other on the benzene ring.

In contrast, according to the present invention, the mesitylene ring, which is readily available in the form of bromomesitylene, is used in place of the benzene ring, so that the substituent groups (amine and perfluoroalkyl) have no other choice but be arranged in meta position with respect to each other.

Use of the new fluorinated diamines according to the present invention is a viable route to produce new polyimides with reduced moisture absorption and dielectric constant. Likewise, other polymers based on these diamines, such as for example polyamides, polyureas, and the like may be made. In addition, the diamines of the present invention may be used in other applications, such as for example curing agents for epoxies, and the like.

3. Summary of the Invention

The instant invention is directed to perfluoroalkyldiaminomesitylene and polymers, preferably polyimides, or other compositions of matter, made therefrom.

More particularly, this invention pertains to a composition of matter comprising the structure:

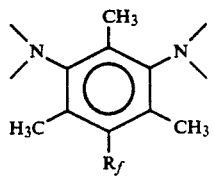

wherein Rf is a perfluoroalkyl group.

It also pertains to a composition of matter having the structure:

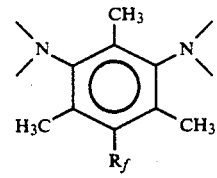

wherein Rf is a perfluoroalkyl group.

Further, it pertains to a composition of matter having repeating units of the structure:

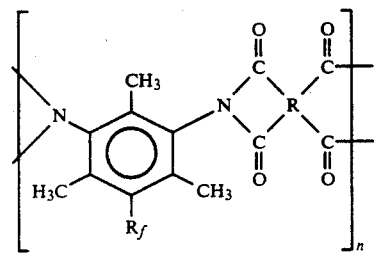

wherein Rf is a perfluoroalkyl group, R is a tetravalent radical and n is an integer.

The perfluoroalkyl group Rf, according to this invention, contains preferably 1-20, more preferably 4-16, and even more preferably 6-20 carbon atoms. Of special interest are compositions, wherein Rf contains 6 or 8 carbon atoms, due to adequately high fluorine content for many end-uses, and better availability of raw materials. Regarding R, it is preferred that it comprises aromatic functionality (aromatic rings) for better thermal-oxidative stability, as well as fluorinated groups, also for better thermal-oxidative stability, for reduced water absorption, reduced dielectric constant, and the like. Of special interest are polyimides having perfluoroalkyl groups Rf with 6 or 8 carbon atoms, and in which R is

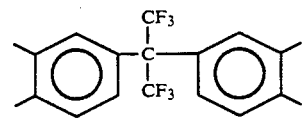

4. Detailed Description of the Invention

The instant invention is directed to perfluoroalkyldiaminomesitylene and polymers, preferably polyimides, or other compositions of matter, made therefrom.

It is desirable that any perfluoroalkylated aromatic diamine intended for use in making polymers, especially for the Electronics Industry, should not have a substitution pattern such that the perfluoroalkyl substituent is in an ortho or para position relative to either of the amine functionalities, since this would result in diminished stability of the monomer. In order to avoid this, the monomers of choice should have a 1,3,5 substitution pattern of the perfluoroalkyl group and the amine groups; that is, they should have the perfluoroalkyl group in a meta position with respect to both amine groups, as aforementioned. Suitable starting materials for preparing perfluoroalkyldiaminobenzenes with this substitution pattern are 1-bromo-3,5-dinitrobenzene and 1-iodo-3,5-dinitrobenzene. These compounds are difficult to prepare, and; they are not available by nitration of iodo- or bromobenzene, and other methods for their preparation are not practical on a commercial scale.

In contrast, nitration of 2-bromomesitylene affords a product having the desired substitution pattern, because the positions on the aromatic ring where nitration would otherwise be likely to occur are blocked by methyl groups 2-perfluoroalkyl-4,6-diaminomesitylene may be prepared by reduction of 2-perfluoroalkyl-4,6-dinitromesitylene, which in turn may be prepared by conversion of 1-iodoperfluoroalkane to perfluoroalkyl copper and reaction of the latter with 2-bromo-4,6-dinitromesitylene, as exemplified hereinafter. The preparation of 2-bromo-4,6-dinitromesitylene may be conducted by methods well known to the art, such as for example Fittig, and Storer, *Liebigs Ann. Chem.*, 147, 1868, 8, Suessenguth, *Liebigs Ann. Chem.*, 215, 1882, 249, and Adams, and Miller, *J. Amer. Chem. Soc.*, 62, 1940, 53.

The perfluoroalkyl group according to this invention contains preferably 1–20, more preferably 4–16, and even more preferably 6–12 carbon atoms.

2-perfluoroalkyl-4,6-diaminomesitylene may be used to form fluorinated polymers, such as for example poly(amic acids), polyamides, polyimides, polyurethanes, polyureas, and the like. It may also be used to make any other compositions of matter that diamines are suitable in being incorporated, and/or wherein the perfluoroalkyl group would be beneficial, such as for example curing agents for epoxies.

The preferred polymers are polyimides, which in this particular case are usually soluble in one or more commonly used solvents, such as for example polar organic solvents, such as sulfoxide type solvents including dimethylsulfoxide, diethylsulfoxide, and the like, formamide type solvents including N,N-dimethylformamide, N,N-diethylformamide, and the like, acetamide type solvents including N,N-dimethylacetamide, N,N-diethylacetamide, and the like, pyrrolidone type solvents including N-methyl-2-pyrrolidone, N-cyclohexyl, 2-pyrrolidone, 1,3-dimethyl-2-imidozolidione, N-vinyl-2-pyrrolidone, and the like, phenolic solvents including phenol, o-, m-, p-cresol, xylenol, halogenated phenol, catechol, and the like, hexamethylphosphoramide, and a number of lactones including γ-butyrolactones. These solvents may be used alone or as a mixture. Partial use of aromatic hydrocarbons such as xylene, toluene, and the like, is also possible.

In addition, applicants have observed that considerably higher molecular weight polymers may result by going directly to the polyimide than by first forming the poly(amic acid) and using it for later imidization.

Examples of preferable dianhydrides, which may be used with 2-perfluoroalkyl-4,6-diaminomesitylene are 2,2'-bis(3,4-dicarboxyphenyl)hexafluoropropane; pyromellitic dianhydride; 1,4,5,8-naphthalene tetracarboxylic dianhydride; 2,3,6,7-naphthalene tetracarboxylic dianhydride; 3,3', 4,4'-biphenyl tetracarboxylic dianhydride; 1,2,5,6-naphthalene tetracarboxylic dianhydride; 2,2', 3,3'-biphenyl tetracarboxylic dianhydride; 3,3',4,4'-benzophenone tetracarboxylic dianhydride; 2,2-bis(3,4-dicarboxyphenyl) propane dianhydride; bis(3,4-dicarboxyphenyl) sulfone dianhydride; 3,4,9,10-perylene tetracarboxylic dianhydride; 1,1-bis-(2,3-dicarboxyphenyl)ethane dianhydride; 1,1-bis-(3,4- dicarboxyphenyl)-ethane dianhydride; bis-(2,3-dicarboxyphenyl)methane dianhydride; bis-(3,4-dicarboxyphenyl)methane dianhydride; oxydiphthalic dianhydride; 9-phenyl-9-trifluoromethyl)xanthene-2,3,6,7-tetracarboxylic dianhydride; 9,9-bis-(trifluoromethyl)xanthene tetracarboxylic dianhydride; 12, 14-(R)$_2$-12, 14-(Rf)$_2$-12H,14H-5,7-dioxapentacene-2,3,9,10-tetracarboxylic acid dianhydride (wherein R is selected from the group consisting of aryl, substituted aryl, and perfluoroalkyl, and R$_f$ is perfluoroalkyl); and the like.

| | GLOSSARY |
|---|---|
| CHP: | N-cyclohexyl-2-pyrrolidone |
| DMAC: | Dimethylacetamide |
| DSC: | Differential Scanning Calorimetry |
| 6FDA: | 2,2'-bis(3,4-dicarboxyphenyl)-hexafluoropropane |
| GPC: | Gel Permeation Chromatography |
| NMP: | N-methyl-2-pyrrolidone |
| Rf6DAM: | 2-Perfluorohexyl-4,6-diaminomesitylene |
| Rf8DAM: | 2-Perfluorooctyl-4,6-diaminomesitylene |
| THF: | Tetrahydrofuran. |

In the following examples all parts and percentages are by weight unless otherwise indicated.

EXAMPLE 1

Preparation of 2-Perfluorohexyl-4,6-dinitromesitylene

A one-liter flask was flushed with argon and charged with 119.5 g (0.268 mole) of 1-iodoperfluorohexane, 34.1 g (0.536 mole) of copper powder, and 400 ml of dimethylsulfoxide. The mixture was stirred and heated under an argon atmosphere to 102° C., and held and that temperature for two hours, to effect conversion of the 1-iodoperfluorohexane to perfluorohexyl copper(I).

The reaction mixture was cooled to 60° C., and to it was added 55.0 g (0.190 mole) of 2-bromo-4,5-dinitromesitylene. With continued stirring under argon, the mixture was heated for about 18 hours at 70° C., and then for three hours at 100° C. The reaction mixture was diluted with an approximately equal volume of water, and the precipitated solids were collected by suction filtration. The filtrate was extracted with methylene chloride, and solvent was removed from the extracts by rotary evaporation at reduced pressure. The residue and the filtered solids were combined and extracted with one liter of acetone in a Soxhlet extraction apparatus. The resulting acetone solution was cooled to about 0° C. to effect crystallization of the extracted product. The crystalline solid was collected by suction filtration and dried to afford 65.6 g (65% of theory) of 2-perfluorohexyl-4,6-dinitromesitylene, m.p. 125°–129° C.

EXAMPLE 2

Preparation of 2-Perfluorohexyl-4,6-diaminomesitylene

A 65.6 g (0.124 mole) portion of 2-perfluorohexyl-4,6-dinitromesitylene from Example 1 was combined with 600 ml of anhydrous ethyl alcohol and 6.5 g of 5% palladium on carbon. The mixture was charged into an autoclave, then heated at 100° C for seven hours while agitating under a hydrogen pressure of 500 psig.

The hydrogenation mixture was cooled and filtered, and solvent was removed from the filtrate by rotary evaporation at reduced pressure to leave a residue of 58.5 g of crude product. This was recrystallized from one liter of hexane to afford 40.0 g (0.085 mole, 69% of theory) of crystalline product, 2-perfluorohexyl-4,6-diaminomesitylene, m.p. 142°–145° C.

EXAMPLE 3

Preparation of 2-Perfluorooctyl-4,6-dinitromesitylene

A one-liter flask was flushed with argon and charged with 146.3 g (0.268 mole) of 1-iodoperfluorooctane, 34.1 g (0.536 mole) of copper powder, and 400 ml of dimethylsulfoxide. Under an argon atmosphere, the mixture was stirred and heated to 102° C., and held and that temperature for 1.25 hour to effect conversion of the 1-iodoperfluorooctane to perfluorooctyl copper(I).

The reaction mixture was cooled to below 70° C., and to it was added 55.0 g (0.19 mole) of 2-bromo-4,5-dinitromesitylene. The mixture was heated overnight at 68° C., under argon, with continued stirring. A 500-ml portion of water, heated to 60° C., was then added, and the resulting mixture was filtered. The solids were extracted thoroughly with methylene chloride and 1,1,2-trichlorotrifluoroethane. The combined organic extracts were washed with water and dilute sodium bisulfite solution, dried over magnesium sulfate, and solvent was removed by rotary evaporation at reduced pressure, to leave 94.2 g (79% of theory) of crude product, 2-perfluorooctyl-4,6-dinitromesitylene. This was recrystallized from methanol and acetone to give 89.2 g of purified product (75% of theory), m.p. 139°–142 C.

EXAMPLE 4

Preparation of 2-Perfluorooctyl-4,6-diaminomesitylene

A 76.9 g (0.122 mole) portion of 2-perfluorooctyl-4,6-dinitro-mesitylene (prepared as described in Example 3) was combined with 600 ml of anhydrous ethyl alcohol and 7.6 g of 5% palladium on carbon. The mixture was charged into an autoclave, then heated at 100° C. for seven hours while agitating under a hydrogen pressure of 500 psig.

The hydrogenation mixture was cooled and filtered, and solvent was removed from the filtrate by rotary evaporation at reduced pressure to leave a residue of crude product. This was digested in hot hexane, treated with decolorizing charcoal, filtered, and the solution cooled to obtain 37.2 g (0.065 mole, 54% of theory) of crystalline product, 2-perfluorooctyl-4,6-diaminomesitylene, m.p. 144.5°–146.5° C.

EXAMPLE 5

6FDA/Rf6DAM

Into a 100 ml reaction kettle equipped with a mechanical stirrer, a Dean-Stark trap, and a nitrogen inlet and outlet, were charged 3.8947 g (8.7671 mmoles) 6FDA and 4.1053 g (8.7671 mmoles) of Rf6DAM. These monomers were then dissolved in 24 ml of anhydrous NMP and 5 ml of anhydrous N-cyclohexylpyrrolidone (CHP). The solution was stirred for about 2 hours at room temperature, 1 ml additional CHP was added, and then the temperature was gradually increased to 180°–190° C. to allow imidization to proceed. The reaction was held at 180–190 overnight (~18 hours), after which time a moderate viscosity increase was noted in addition to a darkening of the solution. The reaction was then allowed to slowly cool to room temperature, and a higher viscosity phase separated from the reaction solvent. Heating the solution to about 100° C. homogenized the solution; it was then precipitated hot into methanol. The polymer was then filtered and dried, redissolved in chloroform, and once again precipitated into methanol. It was recovered by filtration and then dried under vacuum with nitrogen bleed. Recovered yield was 7.2 g and the polymer was also found to be soluble in hot DMAC and hot m-cresol, and at room temperature in acetone. The resulting polyimide exhibited a Mn of 22600 and an Mw of 46000 (Mw/Mn=2.04) when measured by gel permeation chromatography in DMAC+p-toluenesulfonic acid (1 g/4 l DMAC) at 135° C. versus polystyrene standards. H-NMR analysis in CDC13 was consistent with the proposed polyimide structure with resonances due to the methyl groups from mesitylene moieties appearing at 2.0 and 2.3 ppm, and those from 6FDA moieties appearing at 7.95 and 8.1 ppm. DSC analysis revealed a Tg of 310° C. (10° C./min, 2nd scan).

EXAMPLE 6

6FDA/Rf6DAM

Into a 100 ml reaction kettle equipped with a mechanical stirrer, a Dean-Stark trap, and a nitrogen inlet and outlet, were charged 3.8947 g (8.7671 mmoles) 6FDA and 4.1053 g (8.7671 mmoles) of Rf6DAM. These monomers were then dissolved in 24 ml of anhydrous N-cyclohexylpyrrolidone (CHP) and 0.4 ml of isoquinoline. The solution was stirred overnight (~18 hours) at room temperature, a sample was removed for GPC analysis, and then the temperature was gradually increased to 180°–90° C. to allow imidization to proceed. The reaction was held at 180–190 for about 32 hours, after which time only a moderate viscosity increase was noted. Upon cooling, a gel-like material phase separated from the reaction solvent, which redissolved upon addition of about 50 ml of acetone/chloroform. This solution was precipitated into methanol containing a very small amount of hydrochloric acid. Then it was filtered and dried. The polymer was then dissolved in chloroform and then reprecipitated into methanol for further purification, followed by filtration and drying at 80° C. under vacuum with nitrogen bleed. The resulting polyimide exhibited a Mn of 23400 and an Mw of 48900 (Mw/Mn=2.09) when measured by gel permeation chromatography in DMAC+p-toluenesulfonic acid (1 g/4 l DMAC) at 135° C. versus polystyrene standards. This was considerably higher on a relative basis than the GPC molecular weight results obtained for the removed poly(amic acid) sample which gave Mn=7420, Mw=9770 (Mw/Mn=1.3) in a mixed solvent system of DMAC/LiBr/H3PO4/THF at 35° C. versus polystyrene standards.

EXAMPLE 7

6FDA/Rf6DAM

A similar procedure to that given in Example 2 was employed except that 24 ml of distilled m-cresol with 0.4 ml isoquinoline was used a reaction solvent. The polymer was isolated by precipitation from the hot reaction solvent into methanol, filtered and dried, redissolved in chloroform, reprecipitated into methanol and dried under vacuum with nitrogen bleed. The resulting polyimide exhibited a Mn of 30600 and an Mw of 70500 (Mw/Mn=2.31) when measured by gel permeation chromatography in DMAC+p-toluenesulfonic acid (1 g/4 l DMAC) at 135° C. versus polystyrene standards.

EXAMPLE 8

6FDA/Rf6DAM

Into a 100 ml reaction kettle equipped with a mechanical stirrer, a Dean-Stark trap, and a nitrogen inlet and outlet, were charged 3.8947 g (8.7671 mmoles) 6FDA and 4.1053 g (8.7671 mmoles) of Rf6DAM. These monomers were then dissolved in 24 ml of anhydrous NMP and 12 ml of toluene. The Dean-Stark trap was also filled with toluene. The reaction was allowed to proceed under nitrogen for several hours at room temperature, a sample was removed for GPC analysis and was then the reaction was heated via a silicone oil bath to about 150°-160° C. (bath temp.). At this point, the toluene refluxed and was continually returned via the Dean-Stark trap in order to azeotropically remove water generated by imide formation. After several hours, some toluene was removed from the Dean-Stark trap and the reaction was allowed to continue overnight at 160° C. (bath temp). The viscosity had built noticeably overnight and most of the toluene had apparently been removed. Upon cooling to room temperature, a high viscosity phase separated from the reaction solvent. Addition of chloroform to the reaction mixture redissolved the polymer and the solution was then precipitated into methanol to yield a fluffy, fibrous, off-white precipitate which was subsequently filtered and dried. The polymer was then dissolved in chloroform and then reprecipitated into methanol for further purification. The resulting polyimide exhibited a Mn of 42300 and an Mw of 110000 (Mw/Mn=2.6) when measured by gel permeation chromatography (GPC) in DMAC+p-toluenesulfonic acid (1 g/4 1 DMAC) at 135° C. versus polystyrene standards. Comparison of the GPC molecular weight of the polyimide to that of the precursor poly(amic acid) sample (Mn=9700, Mw=13800 in DMAC/LiBr/H3PO4/THF at 35° C. versus polystyrene standards) showed a considerable improvement in relative molecular weight. DSC analysis revealed a Tg of 320° C. (10° C./min, 2nd scan).

EXAMPLE 9

FILM FROM EXAMPLE 8

The polyimide produced in Example 8 was dissolved in butyl acetate (at 25 wt % solids) filtered through a 10 micron filter and spin coated onto 5" silicon wafers. These wafers were then soft-baked by heating to 135° C. for 30 minutes, then heated from room temperature to 200° C. and held at 200° C. for 30 minutes and subsequently heated to 350° C. and held at 350° C. for 1 hour. A 13.7 micron pale yellow polyimide film resulted which had the following tensile properties when measured on an Instron (Crosshead speed=5.080 mm/min): Tensile strength at break=73.8 MPa, % elongation at break=8 and Young's modulus=1.3 GPa. The dried film also exhibited a dielectric constant of 2.4 at 1 MHz and had a linear coefficient of thermal expansion of 92 ppm. Thermogravimetric analysis (TGA) in air from room temperature to 600° C. at 15° C./min showed the onset of weight loss to occur at about 397° C.

EXAMPLE 10

6FDA/Rf8DAM

Into a 100 ml reaction kettle equipped with a mechanical stirrer, a Dean-Stark trap, and a nitrogen inlet and outlet, were charged 3.5100 g (7.9012 mmoles) 6FDA and 4.4900 g (7.9012 mmoles) of Rf8DAM. These monomers were then dissolved in 24 ml of anhydrous NMP and 12 ml of m-xylene. The Dean-Stark trap was also filled with m-xylene. After dissolution of the monomers, the solution was heated via a silicone oil bath to reflux the m-xylene (bath temperature ~ 190° C.) in order to azeotropically remove the water generated by imidization. The reaction was allowed to proceed overnight, then small amount ~ 1 ml of xylene was removed from the Dean-Stark trap and the reaction was continued for about another 7 hours. Upon cooling, a higher viscosity phase separated from the reaction solvent. Addition of a small amount of chloroform and heating to ~ 80° C. rehomogenized the solution which was then precipitated into methanol. The polymer was then redissolved in chloroform, precipitated into methanol, isolated by filtration and dried under vacuum with nitrogen bleed. DSC analysis revealed a Tg of 285° C. (10° C./min, 2nd scan).

EXAMPLE 11

6FDA/Rf8DAM

Into a 100 ml reaction kettle equipped with a mechanical stirrer, a Dean-Stark trap, and a nitrogen inlet and outlet, were charged 3.5100 g (7.9012 mmoles) 6FDA and 4.4900 g (7.9012 mmoles) of Rf8DAM. These monomers were then dissolved in 32 ml of distilled m-cresol and 0.6 ml of isoquinoline. After dissolution, the reaction was heated in a silicon oil bath (bath temperature ~ 200° C., and allowed to proceed overnight (about 22 hours). Upon cooling, a higher viscosity phase separated from the reaction solvent, which redissolved upon dilution with chloroform. The solution was then precipitated into methanol and the polymer was separated by filtration, dried, redissolved in chloroform and reprecipitated into methanol, followed by filtration and drying under vacuum with nitrogen bleed. DSC analysis revealed a Tg of 282° C. (10° C./min, 2nd scan).

What is claimed is:

1. A composition of matter comprising the structure:

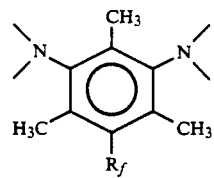

wherein Rf is a perfluoroalkyl group containing from 4 to 16 carbon atoms.

2. The composition of matter as defined in claim 1 having the structure:

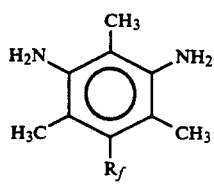

wherein Rf is a perfluoroalkyl group containing from 4 to 16 carbon atoms.

3. A composition of Matter having repeating units of the structure:

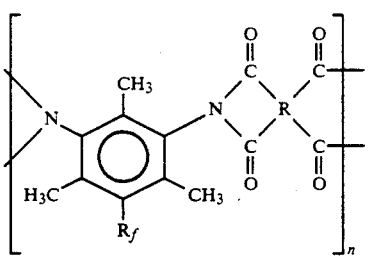

wherein Rf is a perfluoroalkyl group containing from 4 to 16 carbon atoms, R is a tetravalent radical and n is an integer.

4. A composition of matter as defined in claim 3, wherein R comprises fluorinated groups.

5. A composition of matter as defined in claim 4, wherein Rf comprises 6 carbon atoms and R is

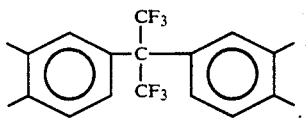

6. A composition of matter as defined in claim 4, wherein Rf comprises 8 carbon atoms and R is

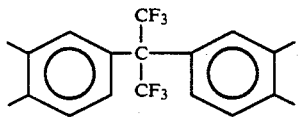

7. A composition of claim 1 wherein Rf contains from 6 to 12 carbon atoms.

8. A composition of claim 2 wherein Rf contains from 6 to 12 carbon atoms.

9. The composition of claim 3 wherein Rf contains from 6 to 12 carbon atoms.

* * * * *